United States Patent [19]

Svanberg

[11] Patent Number: 5,682,665
[45] Date of Patent: Nov. 4, 1997

[54] METHOD FOR MANUFACTURING A DENTAL CURETTE

[76] Inventor: Gunnar K. Svanberg, 2814 NW. 58th Blvd., Cainerville, Fla. 32606

[21] Appl. No.: 556,047

[22] Filed: Nov. 13, 1995

Related U.S. Application Data

[62] Division of Ser. No. 320,746, Oct. 11, 1994, abandoned.

[51] Int. Cl.$^6$ .................................................. B23P 25/00
[52] U.S. Cl. ........................ 29/458; 29/460; 29/527.3; 29/896.1; 433/143
[58] Field of Search .................. 29/458, 460, 527.3, 29/527.5, 896.1; 433/141, 144, 143, 142

[56] References Cited

U.S. PATENT DOCUMENTS

| | | | |
|---|---|---|---|
| 2,677,843 | 5/1954 | Goodman | 433/143 |
| 4,449,934 | 5/1984 | Salam | 433/143 |
| 5,030,091 | 7/1991 | Svanberg | 433/143 |
| 5,040,981 | 8/1991 | Oliva | 433/141 |

FOREIGN PATENT DOCUMENTS

| | | | |
|---|---|---|---|
| 236232 | 9/1987 | European Pat. Off. | 433/143 |

*Primary Examiner*—David P. Bryant
*Attorney, Agent, or Firm*—Saliwanchik, Lloyd & Saliwanchik

[57] ABSTRACT

A method of manufacturing a dental curette having a handle, a shank disposed on one end of the handle, and a cutting blade on the shank, includes the steps of: providing a curette mold having at least a shank portion and a cutting blade portion, injection molding a feedstock into the curette mold to form a molded shank and a molded cutting blade, and attaching a handle to the molded shank. There is likewise disclosed an injection molded dental curette. A coating of extreme hardness may be provided on the cutting edge of the curette to extend the useable life thereof.

12 Claims, 4 Drawing Sheets

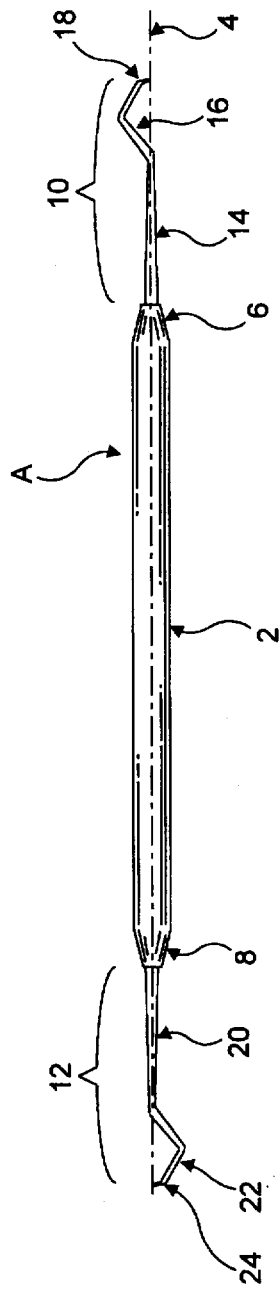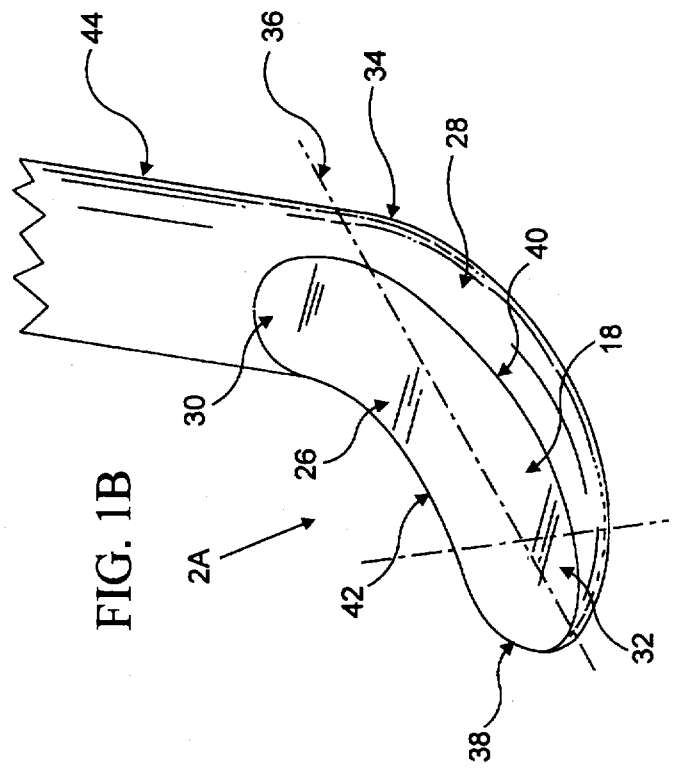
FIG. 1A
FIG. 1B

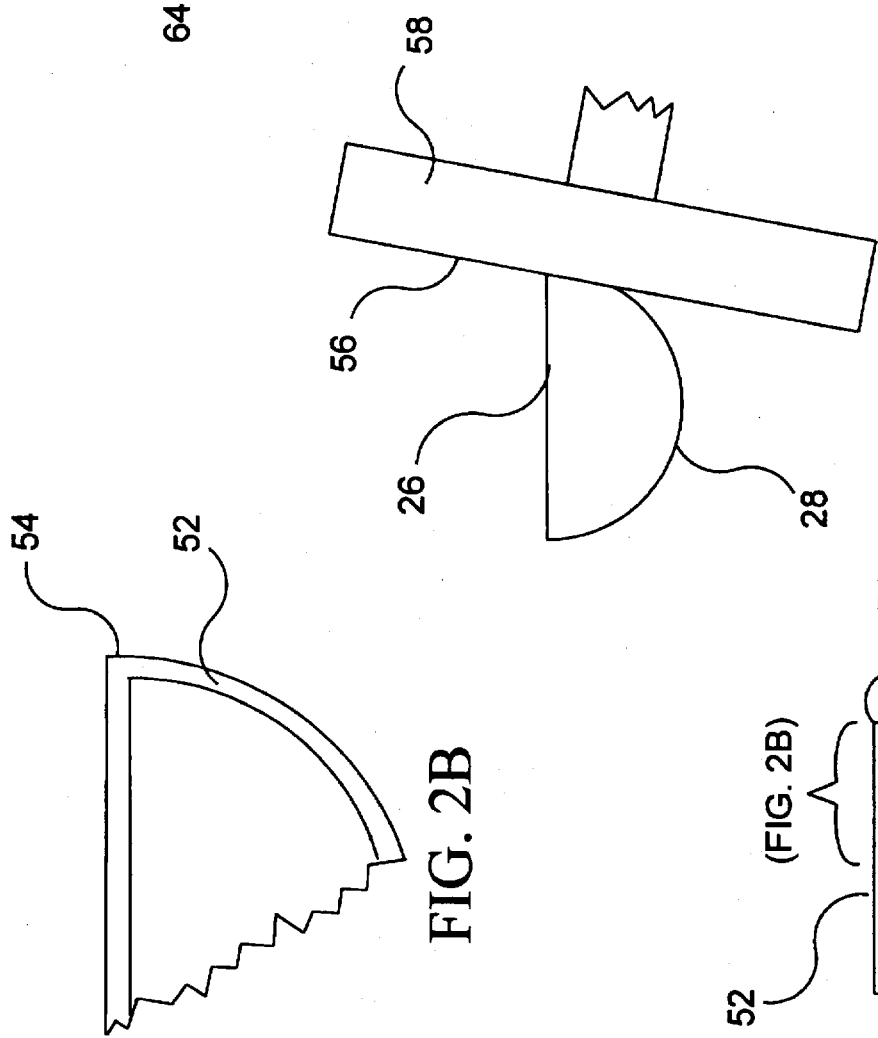

METHOD FOR MANUFACTURING A DENTAL CURETTE

CROSS REFERENCE TO RELATED APPLICATIONS

This application is a divisional of U.S. patent application Ser. No. 08/320,746, filed Oct. 11, 1994, and which is now abandoned.

FIELD OF THE INVENTION

The present invention relates to dental tools and more particularly to a method of manufacturing dental curettes.

BACKGROUND OF THE INVENTION

Scaling and root planing for the removal of calculus and contaminated root cementum are essential procedures in the treatment of periodontal diseases. For this purpose, dental curettes are used for orthogonal cutting of the root surfaces, a process that removes calculus and thin chips contaminated root cementum.

These procedures dull the edge of the curettes, which for proper cutting action has to be sharpened at frequent intervals. Up to now, such sharpening has been done as a freehand procedure with or without guide plates, resulting in edges of inferior sharpness, incorrect edge angles, and serious aberrations from the ideal shape of the cutting blade.

Most curettes on the market are double-ended, i.e., comprise a longitudinal handle with a cutting blade at the distal end of a shank, which is secured to each end of the handle. The handles usually are made out of metal tubing, the surface of which is processed to give different patterns of grooves and ridges to increase the friction when holding the curettes during the scaling and root planing procedures.

The shanks are made from slightly conical metal rods, which are bent manually into various shapes for curettes of different rake angles. As is apparent, bending the shank manually into the desired rake angle is a labor-intensive procedure. It requires the use of a relatively soft metal that has to be tempered or otherwise treated for giving the shank with its cutting blade reasonable hardness. Fairly crude templates are used during the bending of the shanks, which makes the process contingent on the utmost skill of the worker for achieving a reasonable precision of the curette. Despite all these efforts, the accuracy and precision of today's commercially available curettes are not very good, and they get dull after a very short time of scaling and root planing.

After the shanks are bent into the desired rake angle, they are secured to the handle of the curette by crimping, soldering, or other means. Following attachment of the shanks to the handle, the distal end of the shanks is ground to form the cutting blade, again a procedure that requires a skilled worker. All these difficulties in manufacturing dental curettes and the shortcomings of the final product made us look for alternative processes and materials.

OBJECTS AND SUMMARY OF THE INVENTION

It is therefore an object of the present invention to use novel methodologies and technologies for manufacturing dental curettes of extremely high accuracy and precision previously unavailable in the prior art.

It is another object of the present invention to provide a method for fabricating dental curettes by using the injection molding technology. This method of manufacturing enables high-voltage production of geometrically complex instruments of the highest accuracy and precision.

It is yet another object of the present invention to incorporate computer-assisted design (CAD)/completer-assisted manufacturing (CAD) in the protocol for fabricating dental curettes, using CAD for designing the curettes and CAM for fabrication of the molds for subsequent manufacturing of the curette shanks with their cutting blades.

It is a further object of the present invention to coat at least the edge portion of the curette's cutting blade with a compound of extreme hardness, which will make it possible to establish, and if so needed restore, cutting edges of the utmost sharpness and durability.

It is another object of the present invention to determine the optimal thickness and configuration or a coating compound of extreme hardness, covering at least the edge portion of the curette's cutting blade, so that sharpening or the cutting blade will produce an edge of long-lasting sharpness although most of the grinding is on the substantially softer core material of the cutting blade.

It is also the object of the present invention to coat at least the edge portion of the curette's cutting blade with a compound or extreme hardness for producing a cutting edge of long-lasting sharpness, which will allow the selection of a compound for the core portion of the shank with its cutting blade to be based on its resistance to breakage during the scaling and root planing procedure.

It is thus an object of the present invention to develop a compound for the core portion of the shank with its cutting blade that will provide optimal resistance to breakage.

It is also the object off the present invention to mold a compound of extreme hardness into the edge portion of the curette's cutting blade so that sharpening of cutting blades is not needed.

In summary, the novel and essential features of the present invention are: CAD design of dental curettes followed by CAM fabrications of molds for manufacturing dental curettes using the injection molding technology. The edge of the cutting blades is given long-lasting sharpness by either coating the edge portion with a compound of extreme hardness, or molding a compound of extreme hardness into the edge portion of the cutting blades. The following description will exemplify one of many possible protocols for the implementation of these concepts.

1. Computer-aided design/computer-aided manufacturing (CAD/CAM).

The use of CAD will greatly facilitate curette design and so will the use of CAM for manufacturing the molds, which are used in the MIM process for fabricating the shanks with their cutting blade. The use of CAD/CAM in combination with MIM guarantees shanks with a cutting blade of the utmost accuracy and precision, which are made of stainless steel of the highest quality.

2. Metal injection molding (MIM).

This process is well suited to high volume production of geometrically complex parts. It is technically most manageable and most cost-efficient when the part to be manufactured is in the weight range of 1 gram to 25 grams, is complex and of irregular architecture with a major axis of up to 10 centimeters, has a cross-section of about 10 millimeters or less, and is made in quantities of 20,000 or more. Dental curette shanks with their cutting blades more than meet these requirements. Suitable stainless steel alloys and appropriate binders are available on the market, and the shanks can be manufactured with an expected tolerance of 0.1% to 0.3%. If so needed or desired, parts manufactured using the MIM technology can be given supplementary treatment used for modification of wrought metal products such as heat treatment, plating, and machining.

3. Coating and molding.

Technologies are available for the coating of compounds, such as metals and polymers, with compounds of significantly greater hardness. For example, using the MIM technology in our first efforts, the core of the curette's shank with its cutting blade can be made out of stainless steel that has a high resistance to breakage when used for the scaling and root planing procedure, or when accidentally dropped onto a hard surface. The coating of the curet's core element with a layer of a compound of extreme hardness will guarantee an edge or superior sharpness of long durability. Coating with a compound of extreme hardness also makes the sharpening procedure much easier than the sharpening of a cutting blade or solid metal of extreme hardness. A compound or extreme hardness, e.g. ceramic zirconia, can be molded into the edge portion or the curette's cutting blade for an edge or long-lasting sharpness that does not require sharpening.

BRIEF DESCRIPTION OF THE DRAWINGS

FIG. 1A is a side view or a double-ended curette.

FIG. 1B is a fragmentary perspective view of the distal end of the distal portion of the shank with its cutting blade.

FIG. 2A is an enlarged transverse view taken in the direction of the arrows 2A—2A in FIG. 1C. Note the layer of hard metal coating the cutting blade.

FIG. 2B is a further enlargement or a side edge in FIG. 2A

FIG. 2C shows a rotary sharpening element in contact with a side edge of the cutting blade during the sharpening procedure.

FIG. 2D shows the enlarged transverse view of a cutting blade as in FIG. 2A after some sharpening of the edge. Note the removal of the hard coating metal on the lateral base surface.

FIG. 2E is a further enlargement of the sharpened side edge as seen in FIG. 2D

DESCRIPTION OF THE INVENTION

Description of a preferred embodiment

Figures 3A, 3B:
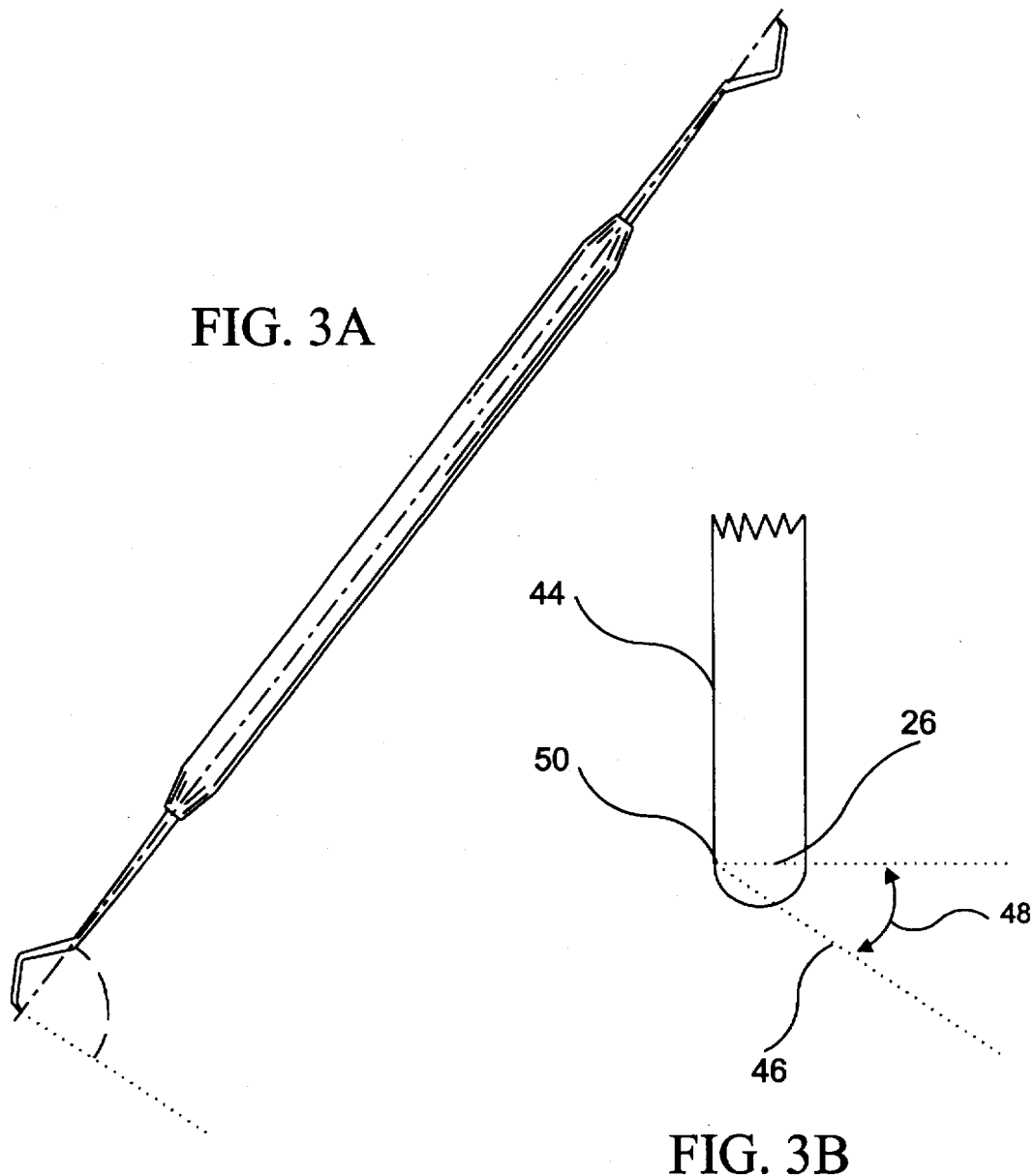
FIG. 3A shows a complete dental curette
FIG. 3B shows a fragmentary enlargement of the distal end of the distal portion or the shank with its cutting blade as shown in the lower part of FIG. 3A.

Turning to FIG. 1A we see a double-ended dental curette according to the present invention. The curette comprises the following major segments. An elongated handle portion 2 extending generally along a major longitudinal axis 4 and terminating at handle end portions 6 and 8.

A pair of shank portions 10 and 12 are provided, each of which extends from a separate one of the handle end portions 6 and 8. Shank portion 10 further comprises a proximal portion 14 and a distal portion 16 terminal tag with a cutting blade 18.

Since the curette is double-ended, the shank portion 12 at opposite end 8 of handle 2 is likewise provided with a proximal portion 20 and a distal portion 22 terminating with a cutting blade 24. Thus, as best seen in FIG. 1A, each shank portion 10 and 12 is a mirror image of the other.

Turning now to FIG. 1B, we see the cutting blade portion of the curette in FIG. 1A in greater detail. The cutting blade portion encompasses a generally flat top surface, the face 26, positioned opposite the rounded bottom surface 28 and extending from upper end 30 to an opposite lower end, toe 32 of the cutting blade 18. Upper end 30 extends beyond bent portion 34 and into distal portion of the shank 16 while the lower end, the toe 32, terminates as a semi-circle on the face 26 or the cutting blade 18. The junction between the face 26 and the rounded bottom surface 28 forms the following cutting edges; A semi-circular edge 38 at the toe of the cutting blade and a pair of side edges 40 and 42 generally extend along the long axis 36 of the cutting blade. As all option, the cutting blade might have only one side edge. Regardless of the configuration of any of the curettes, the arc center of the semi-circular edge at the toe of the cutting blade is always in the long-axis of the curet; see axis in FIGS. 1A and 1B.

Turning to FIG. 3A, we see a complete curette as in FIG. 1A that has been rotated 90 degrees around its long axis relative to the curet seen in FIG. 1A. Therefore, the cutting blade, which in FIG. 1A is seen from the side, is in FIG. 3A and 3B viewed from the toe 32 along its long axis 36, i.e. from the same perspective as in FIG. 2A. FIG. 3B is a fragmentary enlargement of the distal end 44 of the distal portion of the shank 22 with its cutting blade 24 as seen in the lower part of FIG. 3A. Note the long center axis of the instrument and the line 46 perpendicular to the long center axis or the instrument. The angle between this line 46 perpendicular to the long center axis of the instrument and the face of the cutting blade 26 is the curette's rake angle 48 as determined for the side edge further away 50 from the instrument handle.

Figure 4:
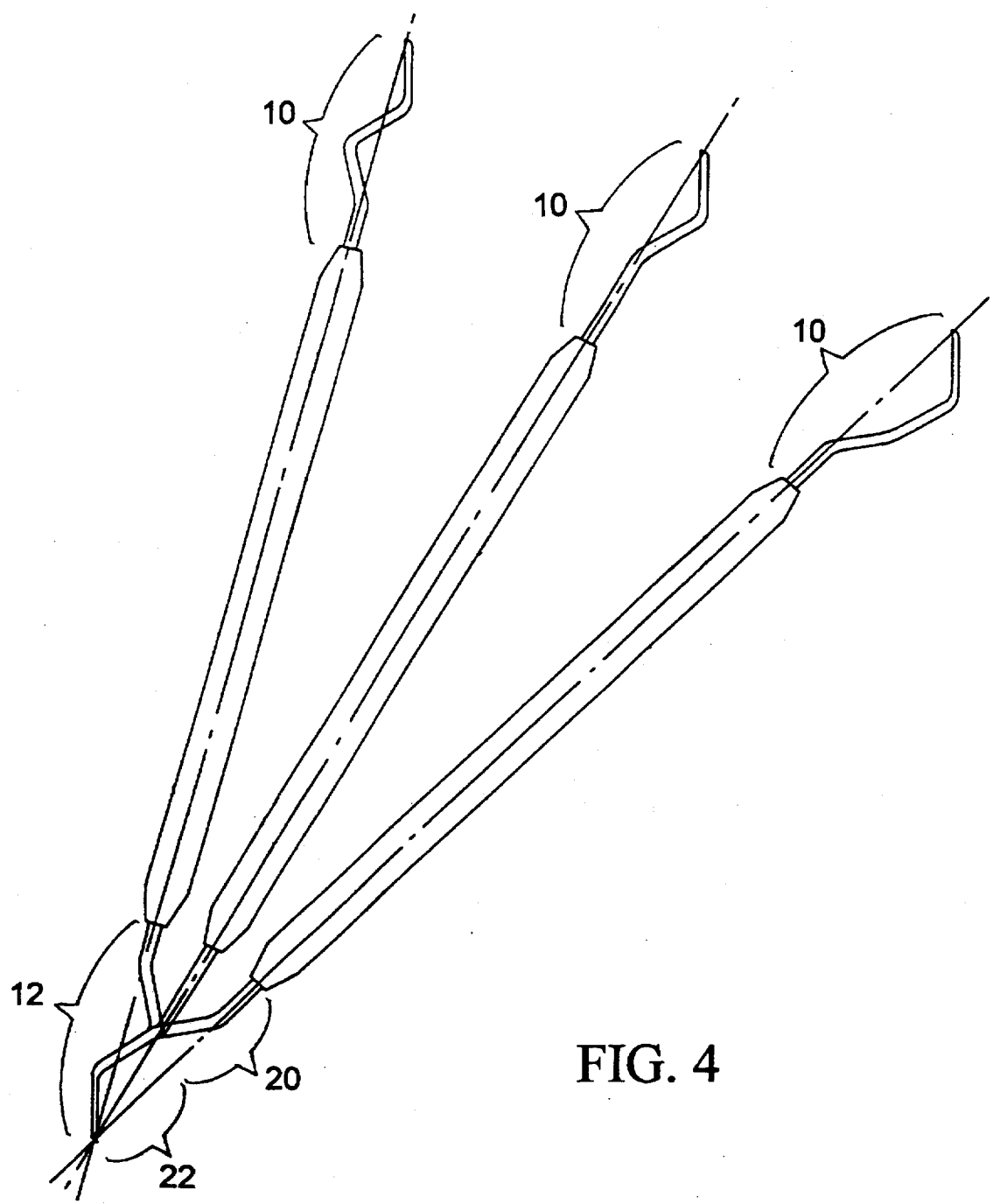
FIG. 4 shows the configuration of three complete curettes of different rake angles having a distal portion of the shank of the same or similar geometry and their proximal portion of the shank of different architecture.

The curettes are designed to provide a series of instruments with different rake angles in regular increments. The rake angle 48 of each instrument, defined as the angle between the face of the cutting blade and the perpendicle to the long center axis of the curette, is determined by the configuration of the shanks 10 and 12, and is indicated by a code on the instrument, e.g. color code. Turning to FIG. 4, we see three curettes of different rake angles viewed from the same perspective as in FIG. 3A. In this example, the distal portion of the shanks, 16 and 22, are identical for the three instruments, and the differences in rake angle are achieved only by differences in the configuration of the proximal portion of the shanks, 14 and 20. For various reasons, the geometry of parts of the distal portion of the shanks, 16 and 22, might also be changed for achieving differences in the rake angle of the curettes, or for better access during the scaling and root planing procedure.

The two cutting blades of one curette are of the same rake angle although, relative to the handle, their positions are mirror images of each other. In other words, when viewed in a working position the two blades are each other's mirror image in that the face of one blade will point to the left, whereas the other will point to the right.

The shank can have various configurations but, when looking on the face of the cutting blade, the arc center of the semi-circular edge at the toe of the cutting blade is always located on the longitudinal center axis 4 of the curet, i.e. the longitudinal center axis of the handle. The general configuration of the lower portion of the shank is typically identical, or close to identical, for all instruments regardless of their rake angle, i.e. the angle between the face of the cutting blade and the line perpendicular to the long center axis of the instrument (handle).

The proximal portion of the shank is given an architecture, shape, and geometric characteristics that are unique for a curette of a specific rake angle, and that also are different for the two mirror image ends of the curette. These design characteristics serve as placement and reference means for the proper placement of the curettes in a dental curette sharpening machine for fully automatic, mechanically guided sharpening of this particular brand of curettes.

Design and manufacturing process

Blueprints of the curettes are generated by computer-aided design (CAD). The manufacturing of the curettes starts by computer-aided manufacturing (CAM) of the molds (tools), which are employed for shaping the curettes using the metal injection molding (MIM) process. This process is well suited to high volume production of geometrically complex parts. It is technically most manageable and most cost-efficient when the part to be manufactured is in the weight range of 1 gram to 25 grams, is complex and of irregular architecture with a major axis of up to 10 centimeters, has a cross-section of about 10 millimeters or less, and is made in quantities of 20,000 or more. Dental curette shanks with their cutting blades more than meet these requirements. Suitable stainless steel alloys and appropriate binders are available on the market, and the parts can be manufactured with an expected tolerance of 0.1% to 0.3%. If so needed or desired, parts manufactured by the MIM technology can be give supplemental treatment used for wrought metal products such as heat treatment, plating, and machining.

The four basic steps for making MIM parts are mixing, molding, debinderizing, and sintering.

1. MIXING: Extremely fine (typically less than 10 microns) prealloyed metal powders are used in the injection molding manufacturing process. A preferred metal alloy powder according to the present invention is commercially available as 17-4 PH Stainless Steel (Metal Powders Products, Inc., Indianapolis, Ind.). By weight, this stainless steel alloy comprises 15.5% to 17.5% chromium, 3% to 5% nickel, 3% to 5% copper, up to 1% manganese, 0.15% to 0.45% cadmium and tantalum, up to 0.03% sulphur, up to 0.04% phosphorus, up to 0.07% carbon, and balance iron. Other metal and alloy compositions are within the scope of the present invention as long as the selected metal powder is suitable for the injection molding process. As can be appreciated, other powders such as ceramics and thermoplastics are within the scope of the present invention.

The metal alloy powder is hot mixed or otherwise blended with a thermoplastic binder, wax, and lubricant. The organic binder may be selected from the group including ethylenevinyl acetate copolymer, polyethylene, atactic polypropylene, polystyrene, polybutyl methacrylate, paraffin wax, carnauba wax, or the like. The blending or mixing of the metal alloy powder with the organic binder may be conducted in accordance with blending methods known in the art. For example, the metal powder and the organic binder may be hot mixed to produce a thick homogenous blend, which is subsequently cooled and granulated to produce a feedstock. Mixing may be achieved within a pressure type kneader or using a screw-type injection press as is known in the plastics industry. This mass is then cooled and finely granulated, and the resulting feed stock is inventoried for production use.

2. MOLDING: Molding is performed in a standard injection molding machine. In this machine, the feedstock is first heated until it is able to flow, then injected under relatively low pressure into the mold cavities. The organic binder in the feedstock makes the mixture flow much more easily thereby ensuring that the corners and undercuts of the mold are sufficiently filled, the allowed to cool and solidify, and are finally ejected as an intricately shaped parts. The parts are allowed to cool and solidify, and then ejected. These "green" parts are loaded onto fixtures for the remainder or the batch processing.

3. DEBINDERIZING: The green parts first enter the debinderizer (a low temperature oven), which sequentially removes most of the various binders from the parts by evaporation leaving behind fully oxidized "brown" parts. The debinderizer utilizes high air flow to sweep the parts and mechanical traps to collect condensates. Because of the complex run profile of temperature ramps and soak times, the entire sequence is microprocessor controlled.

4. SINTERING: The final and most critical step is performed by the high temperature process reactor, where the material assumes its final properties and dimensions. A microprocessor controls a complex run profile of temperatures, times, and internal oven atmospheres. A combination of reactive and inert gases is used to tailor the atmosphere to the special requirements or each process sequence. The five basic sequences are: Purge, decarburization, reduction, sinter, and cool down. During sintering, when temperatures approach 85% of the alloy's melting point (approximately 1100° C. to 1300° C.), the metal powders diffuse, densification occurs, and the parts shrink. Since the size and the shape or the original powder particles are rigidly controlled, the shrinkage is uniform along all axes and therefore very predictable. As a result, the finished parts retain the original complex shape of the molded green parts, and very close tolerances can be achieved (0.1% to 0.3%). Shrinkage of the molded parts to their final and fully sintered state ranges from 15% to 25% depending upon what alloy is being used. The tooling, of course, must be precisely oversized and compensated so that the sintered part shrinks to the desired dimensions.

Injection molding according to the present invention produces a dental curet at or near theoretical density. Parts having a complex form are readily produced with high dimensional accuracy and precision that heretofore has not been possible by conventional processes.

SECONDARY OPERATIONS. If so desired, parts manufactured by the MIM technology can be further treated using processes such as tumbling for polishing, milling, drilling, honing, and plating. In our application of the MIM technology, at least the edge portion of the curette's cutting blades will be coated with a metal of extreme hardness, which makes it possible to give the cutting blade a very sharp edge of the utmost durability.

One such compound (ME92 Electrolizing, Inc., Providence, R.I.) is a USP Class VI certified high chromium composite providing a surface hardness of Re80. ME92 is applied directly to the stainless steel with no intermediate layering. Its unique molecular bonding to stainless steel is absolute and the coating will not chip, flake, or peel. ME92 can be bent, twisted, flexed, or impacted without separating from the stainless steel. Coating of stainless steel with ME92 increases wear-life and the sharpness of cutting edges of stainless steel instruments. However, it is within the scope of the present invention to coat at least the edge portion of the curette's cutting blades with a compound of extreme hardness, or mold a compound of extreme hardness into at least the edge portion of curette's cutting blades, e.g. ceramic zirconia and industrial diamonds.

There are several possible protocols for manufacturing the dental curettes using the MIM technology. The shanks might be fabricated separately and then secured to the instrument handle, which is either manufactured by the MIM procedure or by the conventional process starting with metal tubing or a rod-shaped polymer compound. Manufacturing the curette comprising the handle and the two shanks with their cutting blade as a one-piece part using injection molding is also considered;

Coating at least the edge portion of the curette's cutting blades with a compound of extreme hardness has several advantages. Turning to FIG. 2A, we see a cross-section of a cutting blade at arrows 2A in FIG. 1B, which is taken in a plane that is perpendicular to the longitudinal axis of the cutting blade. This blade has never been sharpened, and a coating 52 of the compound of extreme hardness can be seen at the entire perimeter of the cutting blade. An enlargement of one of the side edges 54 in FIG. 2A is shown in FIG. 2B, which reveals that the coating 52 is intact at the edge portion 54 of the blade.

During the sharpening procedure, the grinding surface 56 of the sharpening element 58 is applied to the edge portion at an angle to the face 26 of the cutting blade as seen in FIG. 2C. The grinding of the side portion of the cutting blade's bottom surface 28 will restore a sharp edge of proper geometry 60 as seen in FIG. 2D. The enlargement of the sharpened edge seen in FIG. 2E also shows that the coating has gradually been ground away 62 during repeated sharpening procedures. The functional cutting edge is still made out of the hard coating compound and always will be following any number of sharpening procedures.

The advantage of a cutting blade with a layer of a compound of extreme hardness over a cutting blade of solid compound of extreme hardness is that, during the sharpening of the coated instrument, most of the grinding occurs on the much softer core metal 64 as seen in FIG. 2E. When sharpening a cutting blade or solid compound of extreme hardness, all grinding is on the compound of extreme hardness. When coating the cutting blade with a compound of extreme hardness, the core metal is selected for its ability to resist breakage during the scaling and root planing procedure, or when accidentally being dropped on a hard surface. It can therefore be advantageous to have dental curettes manufactured the conventional way coated with a compound of extreme hardness.

Molding a compound of extreme hardness into the edge portion of the curette's cutting blades is another of many designs for increasing the durability of the cutting edge, and industrial diamond or ceramic circonia are among the suitable materials.

While this invention has been described as having preferred design, it is understood that it is capable of further modifications, uses and/or adaptations following the general principles of the invention and including such departures from the present disclosure as come within known or customary practice in the art to which the invention pertains, and as may be applied to the essential features set forth, and fall within the scope of the invention or the limits of the appended claims.

I claim:

1. A method of manufacturing a dental curette, the curette having a handle including a distal end and a proximal end, the proximal end of a shank disposed on at least one of said ends of said handle, and a cutting blade disposed on the distal end of said shank, said method including the steps of:
   a) providing a curette mold with a shank portion, said shank portion having a cutting blade portion disposed on the distal end of said shank portion;
   b) injection molding a feedstock into said curette mold to form an injection molded shank and cutting blade of unitary construction; and,
   c) attaching the proximal end of said shank to a handle.

2. A method as defined in claim 1, including the steps of:
   a) providing said curette mold with a handle portion disposed on the proximal end of said shank portion, said shank portion having a cutting blade portion disposed on said distal end of said shank portion; and,
   b) injection molding a feedstock into said curette mold to form an injection molded curette of unitary construction.

3. A method as defined in claim 1, further comprising the steps of:
   a) coating at least an edge portion of the injection molded cutting blade with a coating compound, said coating compound having a hardness greater than the hardness of the compound of said injection molded cutting blade;
   b) applying said coating compound in a layer thinner than the thickness of said injection molded cutting blade;
   c) whereby, during sharpening of said cutting blade, most of the grinding occurs on said injection molded compound of said cutting blade, said injection molded compound being of lesser hardness than said coating compound.

4. A method as in claim 1, further including the step of:
   a) molding at least an edge portion of the injection molded cutting blade with a second compound, said second compound having a hardness substantially greater than the hardness of the injection molded compound.

5. A method of manufacturing a dental curette, the curette having a handle including a distal end and a proximal end, the proximal end of a shank disposed on at least one of said ends of said handle, and a cutting blade disposed on the distal end of said shank, said method including the steps of:
   a) providing a curette mold with a shank portion, said shank portion having a cutting blade portion disposed on the distal end of said shank portion;
   b) metal injection molding a feedstock into said curette mold to form a metal injection molded shank and cutting blade of unitary construction; and,
   c) attaching the proximal end of said shank to a handle.

6. A method as defined in claim 5, including the steps of:
   a) providing said curette mold with a handle portion disposed on the proximal end of said shank portion, said shank portion having a cutting blade portion disposed on the distal end of said shank portion; and,
   b) metal injection molding a feedstock into said curette mold to form a metal injection molded curette of unitary construction.

7. A method as defined in claim 5, further comprising the steps of:
   a) coating at least an edge portion of the metal injection molded cutting blade with a compound, said coating compound having a hardness greater than the hardness of said metal injection molded cutting blade;
   b) applying said coating compound in a layer thinner than the thickness of said metal injection molded cutting blade;
   c) whereby, during sharpening of said cutting blade, most of the grinding occurs on said metal injection molded compound of said cutting blade, said metal injection molded compound being of lesser hardness than said coating compound.

8. A method as in claim 5, further including the step of:
   a) molding at least an edge portion of the metal injection molded cutting blade with a second compound having a hardness substantially greater than the hardness of the metal injection molded compound.

9. A method of manufacturing a dental curette, the curette having a handle including a distal end and a proximal end, a shank disposed on at least one end of said handle, and a cutting blade disposed on the distal end of said shank, said method including the steps of:
   a) using computer-assisted design for generating blueprints of a curette;
   b) using computer-assisted manufacturing for generating a curette mold with at least one shank portion, said shank portion having a cutting blade portion disposed on the distal end of said shank portion;
   c) injection molding a feedstock into said curette mold to form an injection molded shank and cutting blade of unitary construction; and,
   d) attaching the proximal end of said shank to a handle.

10. A method as defined in claim 9, including the steps
   a) using computer-assisted design for generating blueprints of a curette;
   b) using computer-assisted manufacturing to generate a curette mold with a handle portion disposed on the proximal end of said shank portion, said shank portion having a cutting blade portion disposed on said distal end of said shank portion; and,
   c) injection molding a feedstock into said curette mold to form an injection molded curette of unitary construction.

11. A method of manufacturing a dental curette, the curette having a handle including a distal end and a proximal end, a shank disposed on at least one end of said handle, and a cutting blade disposed on the distal end of said shank, said method including the steps of:
   a) using computer-assisted design for generating blueprints of a curette;
   b) using computer-assisted manufacturing for generating a curette mold with at least one shank portion, said shank portion having a cutting blade portion disposed on the distal end of said shank portion;
   c) metal injection molding a feedstock into said curette mold to form a metal injection molded shank and cutting blade of unitary construction; and,
   d) attaching the proximal end of said shank to a handle.

12. A method as defined in claim 11, including the steps of:
   a) using computer-assisted design for generating blueprints of a curette;
   b) using computer-assisted manufacturing to generate a curette mold with a handle portion disposed on the proximal end of said shank portion, said shank portion having a cutting blade portion disposed on said distal end of said shank portion; and,
   c) metal injection molding a feedstock into said curette mold to form a metal injection molded curette of unitary construction.

* * * * *

UNITED STATES PATENT AND TRADEMARK OFFICE
CERTIFICATE OF CORRECTION

PATENT NO. : 5,682,665
DATED : Nov. 4, 1997
INVENTOR(S) : Gunnar K. Svanberg

It is certified that error appears in the above-identified patent and that said Letters Patent is hereby corrected as shown below:

Column 1, line 20: "chips contaminated" should read --chips of contaminated--.

Column 2, line 2: "high-voltage" should read --high-volume--;

line 5: "completer-assisted" should read --computer-assisted--;

line 16: "or a coating" should read --of a coating--; and line 16: "sharpening or" should read --sharpening of--

Column 3, line 18: "or solid metal" should read --of solid metal--;

line 18: "or extreme" should read --of extreme--;

line 20: "or the curette's" should read --of the curette's--;

lines 20-21, "or long-lasting" should read --of long-lasting--;

line 30: "or a side" should read --of a side--; and line 61: "16 terminal tag with" should read --16 terminating with--.

Col. 4, line 9, "26 or" should read --26 of--; and line 13: "all option" should read --an option--.

UNITED STATES PATENT AND TRADEMARK OFFICE
CERTIFICATE OF CORRECTION

PATENT NO. : 5,682,665
DATED : Nov. 4, 1997
INVENTOR(S) : Gunnar K. Svanberg

It is certified that error appears in the above-identified patent and that said Letters Patent is hereby corrected as shown below:

Column 6, lines 3-4: "remainder or the" should read --remainder of the--;

line 19: "or each process" should read --of each process--; and line 50: "Re80." should read --Rc80.--.

Column 7, line 4: "considered;" should read --considered.--.

Signed and Sealed this

Twenty-fourth Day of February, 1998

Attest:

BRUCE LEHMAN

Attesting Officer      Commissioner of Patents and Trademarks